United States Patent [19]
Yasuda et al.

[11] Patent Number: 6,101,405
[45] Date of Patent: *Aug. 8, 2000

[54] METHOD AND DEVICE FOR POSITIONING A LIVING BODY

[75] Inventors: Nobuyoshi Yasuda; Naoki Yanai, both of Neyagawa, Japan

[73] Assignees: Kurashiki Boseki Kabushiki Kaisha, Okayama; Kyoto Daiichi Kagaku Co., Ltd., Kyoto, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 09/128,479

[22] Filed: Aug. 4, 1998

[30] Foreign Application Priority Data

Jun. 8, 1997 [JP] Japan ................................. 9-211697

[51] Int. Cl.$^7$ ........................................................ A61B 5/00
[52] U.S. Cl. ........................................ 600/310; 600/344
[58] Field of Search .................................. 600/310, 322, 600/323, 335, 340, 344, 415; 378/208; 128/879, 878, 880

[56] References Cited

U.S. PATENT DOCUMENTS

| 4,674,110 | 6/1987 | Eaton et al. ........................ 378/208 |
| 4,927,264 | 5/1990 | Shiga et al. . | |
| 4,982,744 | 1/1991 | Stanec ............................... 128/879 |
| 5,485,856 | 1/1996 | Buckland .......................... 128/879 |
| 5,553,613 | 9/1996 | Parker ............................... 600/322 |

FOREIGN PATENT DOCUMENTS

| 0444934A1 | 9/1991 | European Pat. Off. . |
| 06014906 | 1/1994 | Japan . |
| 08332181 | 12/1996 | Japan . |
| WO94/10901 | 5/1994 | WIPO . |
| WO94/13199 | 6/1994 | WIPO . |
| WO95/04924 | 2/1995 | WIPO . |
| WO97/23159 | 7/1997 | WIPO . |

Primary Examiner—Eric F. Winakur
Attorney, Agent, or Firm—Birch, Stewart, Kolasch & Birch, LLP

[57] ABSTRACT

A method of and a device for positioning an area of a living body to be measured relative to a detecting probe during a biodata measurement with the use of a biodata measuring apparatus designed to irradiate with light the area of the living body by means of the detecting probe then held in contact with the area of the living body, then to detect light transmitted through and/or reflected from the area of the living body, and finally to measure a predetermined biodata within the living body on the basis of a spectrum of the transmitted and/or reflected light. A plurality of local fixing units are utilized for fixing a plurality of predetermined portions of the living body, respectively. The portions of the living body are fixed respectively by the local fixing units during the biodata measurement to thereby fix the area to be measured relative to the positioning device.

8 Claims, 10 Drawing Sheets

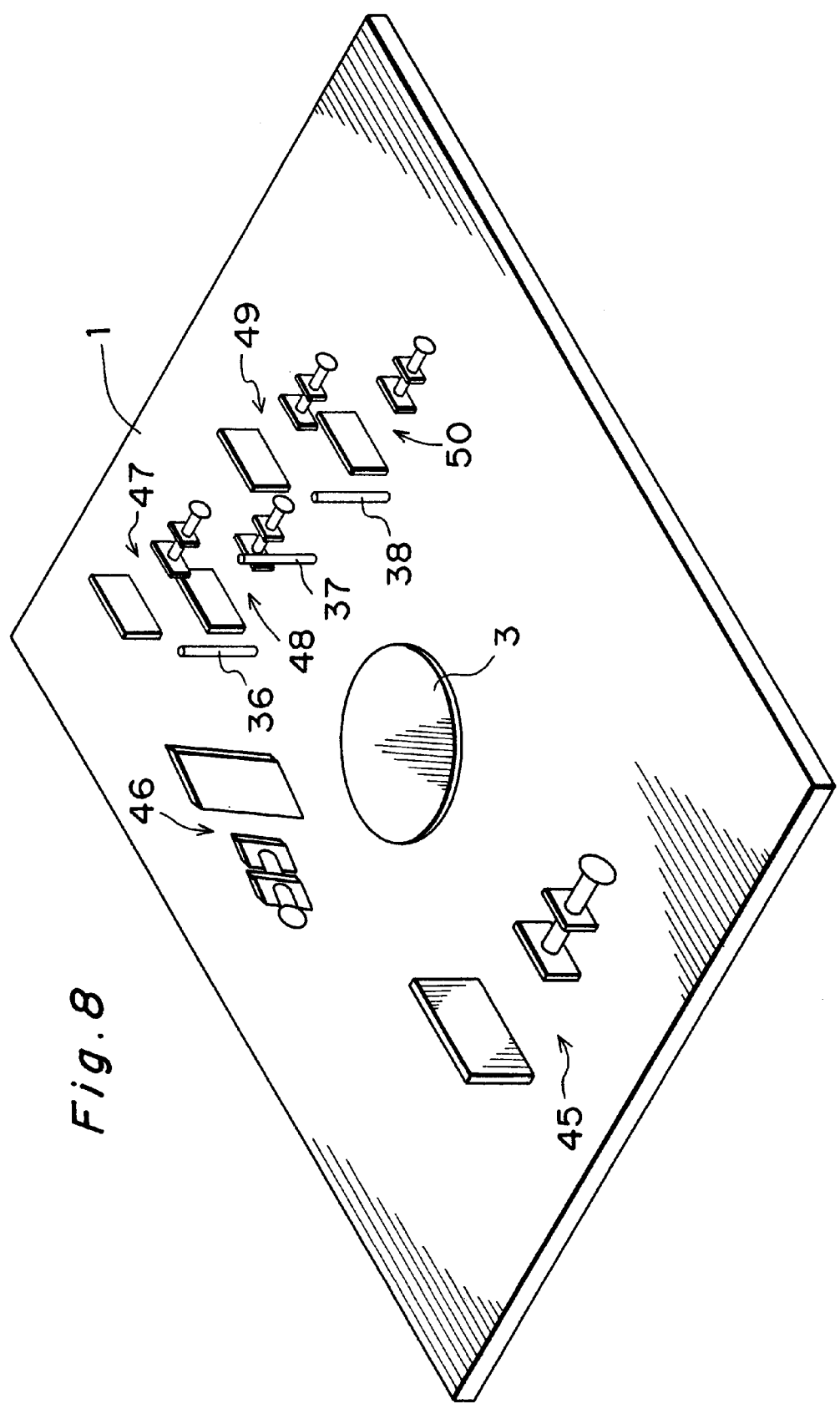

METHOD AND DEVICE FOR POSITIONING A LIVING BODY

BACKGROUND OF THE INVENTION

1. Field of the Invention

The present invention relates to a positioning device for positioning an area of a living body to be measured relative to a detecting probe during a measurement of a biological information with the use of an optical biological information measuring apparatus comprising the detecting probe and, more particularly, to the positioning device utilized in the apparatus to ensure an accurate and exact positioning of the area to be measured relative to the detecting probe.

2. Description of the Prior Art

An optical biological information measuring apparatus for measuring a biological information (which information is hereinafter referred to as a "biodata") from an area of a living body, for example, from a portion of the palm of a hand of a human being, has been well known in the art and is disclosed in, for example, the Japanese Laid-open Patent Publication No. 6-14906. This optical biodata measuring apparatus comprises a detecting probe for irradiating the area of the living body and also for receiving rays of light transmitted through and/or reflected from the area of the living body, and an optical measuring system for measuring or analyzing spectra of the transmitted and/or reflected light to provide the biodata of interest based on those spectra. When this optical biodata measuring apparatus is utilized to measure the biodata, conditions under which the biodata measurement is carried out are required to be kept uniform and consistent throughout the cycle of biodata measurement. So far as the inventors of the present invention have studied, if a portion of the palm of a hand is used as an area to be measured during measurement of the glucose content with the use of the optical biodata measuring apparatus, 1 mm displacement of the area to be measured relative to the detecting probe is suspected to result in variation of the measured glucose content in a quantity equal to or higher than 15 mg/dl.

In view of the above, when the prior art optical biodata measuring apparatus is utilized, the area to be measured is fixedly held in contact with the detecting probe by the use of, for example, a clip or double-sided adhesive tape.

However, the use of the clip or the double-sided adhesive tape to fixedly position the area to be measured relative to the detecting probe has the following problem. Specifically, the biodata measurement is cyclically performed while the detecting probe and the area to be measured are fixed in position relative to each other, the positional relationship between the detecting probe and the area to be measured can be kept constant throughout the repeated biodata measurement However, if the detecting probe once coupled the area to be measured is, after having been once removed, again coupled to the area to be measured during the biodata measurement (i.e., the detecting probe is repeatedly removed and fitted), it has been extremely difficult to align or fix the same area to be measured with the detecting probe. For this reason, with the prior art optical biodata measuring apparatus, variation in measured biodata tends to occur where the biodata measurement is carried out while the detecting probe is frequently removed and fitted to the area being measured.

In view of the above, the optical biodata measuring apparatus has been suggested in, for example, the Japanese Laid-open Patent Publication No. 8-332181, in which a template engageable or alignable with a particular area of the living body to be measured is prepared prior to the biodata measurement and is used during the biodata measurement to accommodate the area to be measured to thereby fix the area to be measured in position relative to the detecting probe while the latter has been arranged in the resultant template. However, this known optical biodata measuring apparatus has the following problem. Specifically, while the positional relation between the detecting probe and the area to be measured can effectively be fixed relative to each other even though the detecting probe is repeatedly removed from and fitted to the area to be measured, the template must be prepared having a shape and/or size complemental to that of the area to be measured for each of living bodies and, therefore, not only is preparation of the template for each living body complicated and time-consuming, but also a substantial amount of time tends to be spent before the biodata measurement starts.

SUMMARY OF THE INVENTION

Accordingly, the present invention has been developed with a view of substantially eliminating the above discussed problems and is intended to provide a means by which when the biodata measurement is to be carried out with the use of the optical biodata measuring apparatus To this end, the present invention provides, in accordance with one aspect thereof a method of positioning an area of a living body to be measured relative to a detecting probe during a biodata measurement with the use of a biodata measuring apparatus designed to irradiate with light the area of the living body by means of the detecting probe then held in contact with the area of the living body, then to detect light transmitted through and/or reflected from the area of the living body, and finally to measure a predetermined biodata within the living body on the basis of a spectrum of the transmitted and/or reflected light. With this method, a plurality of predetermined portions of the living body to be fixed are fixed by the use of local fixing units, one for each of the predetermined portions of the living body, to thereby fix the area to be measured relative to the positioning device.

According to the present invention, since during the biodata measurement, the portions of the living body to be fixed are fixed by the respective local fixing means, the living body can be fixedly retained at a predetermined position or posture. Because of this, even though the detecting probe is frequently removed and then fitted, the positional relation between the detecting probe and the area to be measured can be kept constant and, therefore, the accuracy of biodata measurement with the biodata measuring apparatus can be increased to eventually provide highly accurate biodata.

With this positioning method, since the portions of the arbitrarily chosen living body can be fixed in position by the local fixing means, no preparation of such a template as required in the biodata measuring apparatus disclosed in the previously discussed Japanese Laid-open Patent Publication No. 8-332181 is needed. Accordingly, the biodata measurement can be quickly performed, accompanying a considerable reduction in time needed for preparation for the measurement.

The present invention according to another aspect thereof provides a positioning device for positioning an area of a living body to be measured relative to a detecting probe during a biodata measurement with the use of a biodata measuring apparatus designed to irradiate with light the area of the living body by means of the detecting probe then held in contact with the area of the living body, then to detect light transmitted through and/or reflected from the area of the living body, and finally to measure a predetermined biodata within the living body on the basis of a spectrum of the transmitted and/or reflected light. This device comprises a plurality of local fixing means for fixing a plurality of predetermined portions of the living body, respectively. The portions of the living body can be fixed respectively by the local fixing means during the biodata measurement to thereby fix the area to be measured relative to the positioning device.

According to the present invention, since during the biodata measurement, the portions of the living body to be fixed are fixed by the respective local fixing means, the living body can be fixedly retained at a predetermined position or posture. Because of this, even though the detecting probe is frequently removed and then fitted, the positional relation between the detecting probe and the area to be measured can be kept constant and, therefore, the accuracy of biodata measurement with the biodata measuring apparatus can be increased to eventually provide highly accurate biodata.

With this positioning device, since the portions of the arbitrarily chosen living body can be fixed in position by the local fixing means, no preparation of the hitherto required template is needed and, accordingly, the biodata measurement can be quickly performed, accompanying a considerable reduction in time needed for preparation for the measurement.

Preferably, the local fixing means are repositioned and arranged at desired locations as, for example, stepwise. This is particularly advantageous in that by changing a pattern of arrangement of the local fixing means, the positioning device can accommodate a varying size and/or shape (for example, of the hand) of the living body.

Also, each of the local fixing means preferably comprises a generally C-shaped holder ring for fixedly holding the corresponding portion of the living body, and an arresting pole having a substantially elongated cylindrical configuration and engageable with the corresponding portion of the living body. By so doing, the local fixing means can have a simplified structure sufficient to facilitate fixing of the portions of the living body. Preferably, the holder ring is made of a flexible material so that the corresponding portion of the living body can easily be fixed (i.e., held in position). More specifically, the flexible material may be selected from the group consisting of a rubber material, a metallic material, a soft synthetic resin, a hard synthetic resin and an inorganic plastic material. A shape memory alloy may also be employed for the holder ring, which is particularly advantageous since the alloy is inexpensive enough to reduce the cost of making the holder ring.

Advantageously, the holder ring has a size undersized relative to that of the corresponding portion of the living body that is fixed thereby, so that a tight contact between the corresponding portion of the living body and the holder ring can be ensured during the biodata measurement to thereby assure the constant and consistent positional relation between the detecting probe and the area to be measured.

It is to be noted that the arresting pole is preferably made of a material selected from the group consisting of a rubber material, a metallic material, a soft synthetic material, a hard synthetic material and an inorganic plastic material. Since these materials are relatively inexpensive, the cost required to manufacture the positioning device can be reduced advantageously.

Also, preferably, each of the local fixing means comprises a pressing unit including a fixed plate and movable plate movable close towards the fixed plate to sandwich the corresponding portion of the living body between the fixed and movable plates, and an arresting pole having a substantially elongated cylindrical configuration and engageable with the corresponding portion of the living body. In such case, the living body can be assuredly fixed in position to keep the constant and consistent positional relation between the detecting probe and the area to be measured.

Where the area to be measured is a portion of the palm of a hand of the living body, the holder ring is operable to hold a wrist or one of fingers of the hand and/or the arresting pole is engageable with a bottom of a generally V-shaped crevice delimited between neighboring fingers of the hand. In such case, any possible lateral displacement of the hand can be restrained by the holder rings and any possible displacement of the hand in a forward or rearward direction can be restrained by the arresting poles, to thereby keep the constant and consistent positional relation between the detecting probe and the area to be measured.

In the event that the living body is supported on a plate during the biodata measurement, the use is preferred of a plate temperature control means for controlling a temperature of the plate to a predetermined value. During the biodata measurement, it is well known that the measured biodata tends to vary with change in temperature of the area to be measured to a certain extent. Accordingly, controlling the temperature of the plate to the predetermined value is effective to keep the temperature of the area to be measured at a predetermined temperature, accompanied by increase in accuracy of the eventually obtained biodata.

BRIEF DESCRIPTION OF THE DRAWINGS

The present invention will become readily understood from the following description of preferred embodiments thereof made with reference to the accompanying drawings, in which like parts are designated by like reference numeral and in which:

FIGS. 8 and 9 are views similar respectively to FIGS. 4 and 5, showing a modified form of the positioning device;

DETAILED DESCRIPTION OF THE EMBODIMENTS

Figure 1:
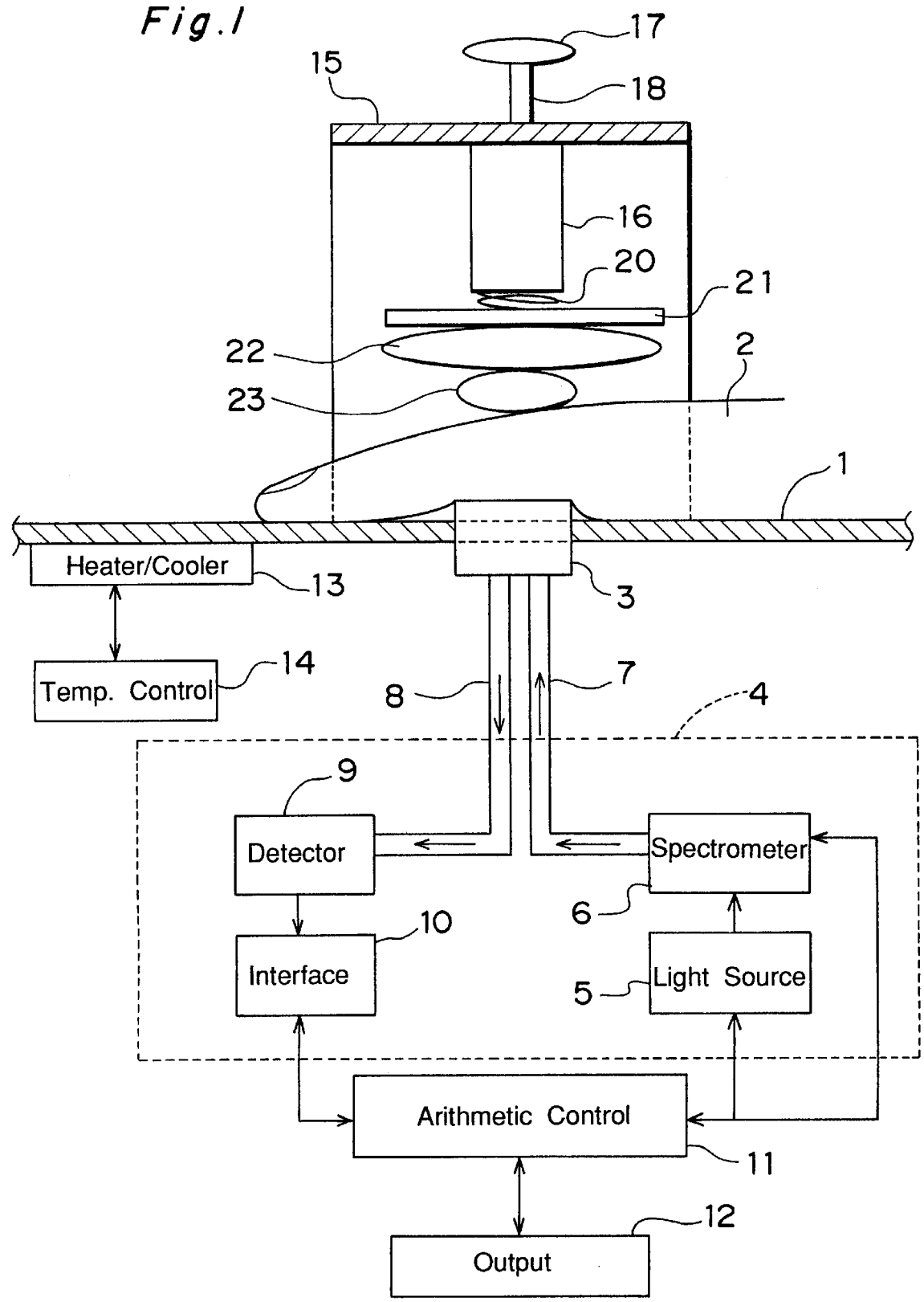
FIG. 1 is a schematic diagram, with a portion shown in section, showing an optical biodata measuring apparatus embodying the present invention.

Referring now to FIG. 1, there is schematically shown a system diagram of an optical biodata measuring apparatus embodying the present invention As shown therein, the optical biodata measuring apparatus is so designed as to measure a biodata such as, for example, the concentration of a biological substance or, particularly, the glucose content from a portion of the palm of a patient's hand. For this purpose, the illustrated optical biodata measuring apparatus basically comprises a heating plate 1 for the support of an area to be measured, which in the illustrated embodiment is the patient's hand 2 with its palm held in contact therewith, a detecting probe 3 for irradiating the area to be measured that is held in contact therewith and also for receiving rays of light transmitted through and reflected from the area to be measured, and an optical measuring system 4 for measuring or analyzing spectra of the transmitted and reflected light to provide the biodata of interest based on those spectra.

The detecting probe 3 is so positioned as to protrude about 5 mm upwardly from an upper surface of the heating plate 1 in order to enhance the contact between the area to be measured and the detecting probe 3.

The optical measuring system 4 includes a light source 5, a spectrometer 6, a transmitting light guide 7 in the form of a bundled optical fiber, a receiving light guide 8 in the form of a bundled optical fiber, a detector 9 and an interface circuit 10. This optical measuring system 4 is so designed and so operable that rays of light emitted from the light source 5 can be analyzed by the spectrometer 6 to provide a measuring light of a predetermined wavelength which is subsequently transmitted to the detecting probe 3 through the transmitting light guide 7. The detecting probe 3 employed in the illustrated embodiment has a light emitting area (not shown) from which the measuring light can be irradiated to illuminate the area to be measured and also has a light receiving area (not shown) for receiving the light transmitted through and reflected from the area to be measured.

The optical measuring system 4 is also operable that the transmitted and reflected light received by the detecting probe 3 can be transmitted through the optical light guide 8 to the detector 9 where the transmitted and reflected light is converted into an electric signal that is subsequently supplied to an arithmetic control unit 11 through the interface circuit 10. The arithmetic control unit 11 operates in response to receipt of the electric signal from the interface circuit 10 to determine the spectrum of the transmitted and reflected light and also to determine the biodata based on the resultant spectrum, the biodata being subsequently outputted to an output unit 12 which may comprise a display and/or a printer.

Generally in the optical biodata measuring apparatus, change in temperature (body temperature) during the measurement tends to be accompanied by change in measurement of the biodata and, accordingly, the accuracy of measurement of the biodata is consequently lowered. In view of this, in the optical biodata measuring apparatus embodying the present invention, the heating plate 1 can be selectively heated or cooled by a heating and cooling unit 13 which is controlled by a temperature control device 14 operable to control the heating and cooling unit 13 to control the temperature of the heating plate 1 to a predetermined temperature.

Figure 11:
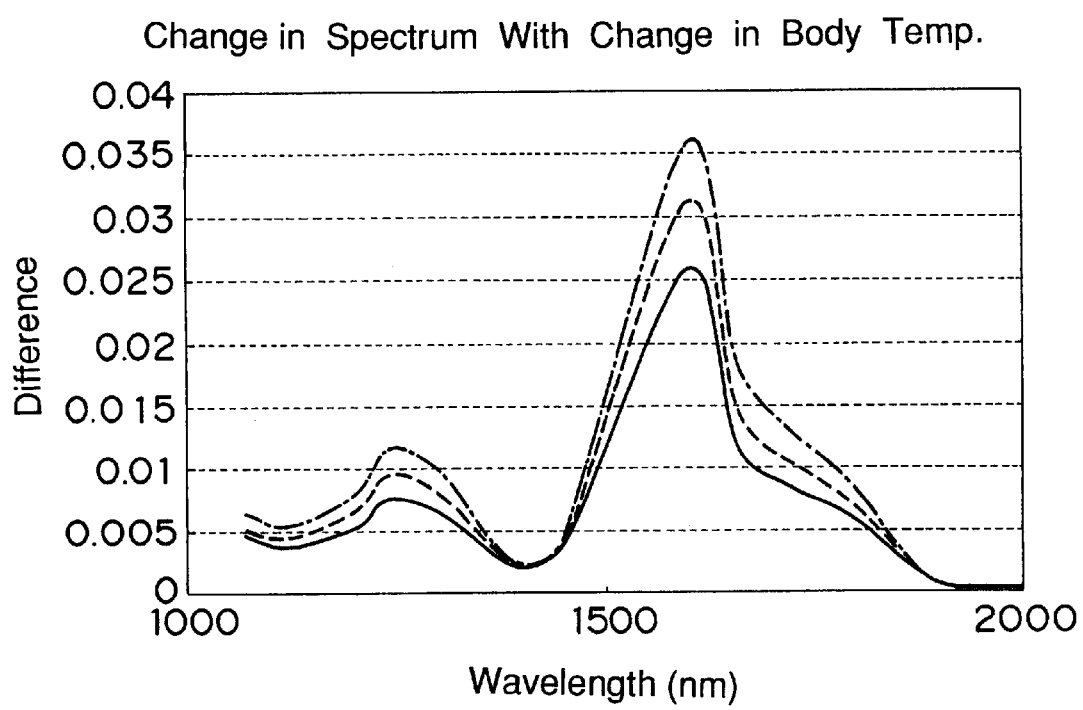
FIG. 11 is a graph showing a characteristic change in measured biodata of a living body with change in body temperature.

Results of measurement of the spectra of the light reflected from the area to be measured when the body temperature was 36° C., 30° C. and 27° C., respectively, are shown in FIG. 11. To obtain these measurement results, optical fibers were used, a portion of the palm of a patient's hand was used for the area to be measured, and the spectrum of the light reflected from that portion of the palm were measured. During the spectral measurement, the temperature in the vicinity of the area to be measured was also measured and is taken as the body temperature. In the graph of FIG. 11, the spectrum measured at the body temperature of 37° C. is taken as a standard spectrum and the spectral strength is expressed in terms of the difference between this standard spectrum and the spectrum measured at each of the other body temperatures. As FIG. 11 makes it clear, the spectral strength changes with change in body temperature. According to the results of measurement shown in FIG. 11, it will readily be seen that the biodata measurement need be performed with the body temperature kept at a predetermined value.

Also, generally in the optical biodata measuring apparatus, change in contact pressure between the area to be measured and the detecting probe 3 during the measurement tends to be accompanied by change in measurement of the biodata to a certain extent and, accordingly, the accuracy of measurement of the biodata is consequently lowered. In addition, unless the area to be measured is held in tight contact with the detecting probe 3, the accuracy of measurement of the biodata tends to be lowered. In view of this, the optical biodata measuring apparatus embodying the present invention is provided with a pressure regulating device for regulating the pressure of contact of the area to be measured with the detecting probe 3 to a predetermined value at all times during the measurement and also for enhancing the contact of the area to be measured with the detecting probe 3.

Figure 2:
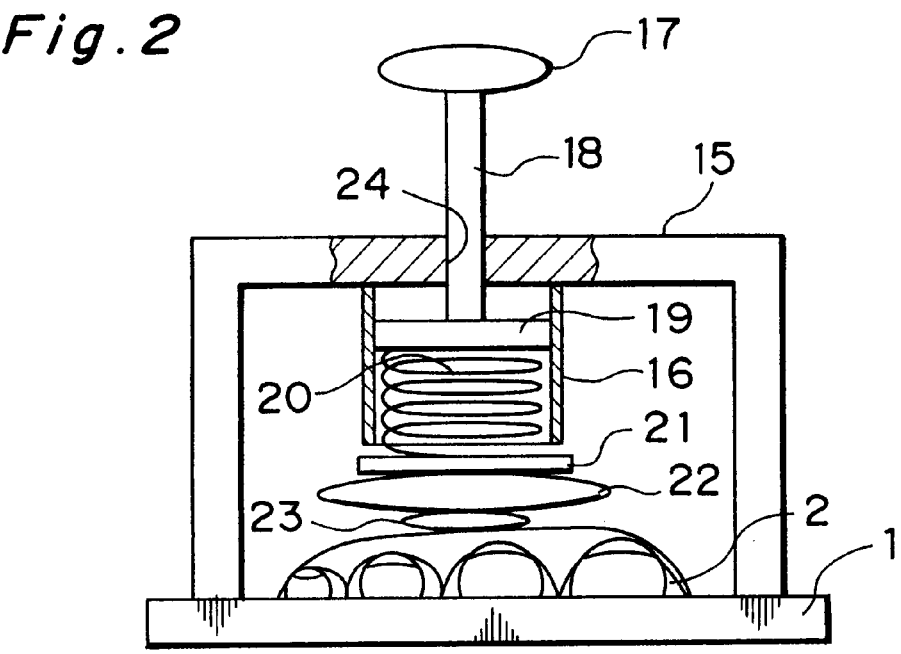
FIG. 2 is a fragmentary sectional view of a portion of a pressure regulating device employed in the biodata measuring apparatus shown in FIG. 1.

Hereinafter, the details and the function of the pressure regulating device will be discussed with particular reference to FIGS. 1 and 2. This pressure regulating device comprises a generally U-shaped box 15 which serves as a housing and which is placed on the upper surface of the heating plate 1 so as to cover the detecting probe 3. More specifically, this box 15 includes a generally rectangular top wall and left and right side walls lying perpendicular to the top wall and is placed on the top surface of the heating plate 1 so as to straddle immediately above the detecting probe 3. Front and rear areas of the box 15 as viewed in a direction conforming to the direction of insertion of the patient's hand 2 are left open so that the patient can insert his hand 2 into a space delimited by the top and side walls of the box 15 so as to place the palm at a predetermined measuring position above the heating plate 1.

A hollow cylindrical member 16 having a longitudinal center axis is fixedly connected to an undersurface of the top wall of the box 15 with the longitudinal center axis lying perpendicular to the undersurface thereof and aligned with the detecting probe 3. As shown in FIG. 2, a portion of the top wall of the box 15 aligned with the longitudinal center axis of the hollow cylindrical member 16 is bored and internally threaded to provide an internally threaded hole 24. An externally threaded screw rod 18 is threadingly inserted in this internally threaded hole 24. This screw rod 18 extends from above the top wall of the box 15 and into the hollow of the cylindrical member 16 through the internally threaded hole 24 and has an upper end formed with an adjustment knob 17. A lower end of the screw rod 18 remote from the adjustment knob 17 and situated inside the cylindrical member 16 has a disc-shaped plate 19 secured thereto. The adjustment knob 17 is provided for an operator's hand to turn the screw rod 18 and is, for this purpose, ergonomically shaped to allow it to be gripped comfortably. It is to be noted that the screw rod 18 has a length greater than the length of the cylindrical member 16.

A coiled compression spring 20 is fitted to an undersurface of the disc-shaped plate 19 with its longitudinal center axis aligned with the longitudinal center axis of the cylindrical member 16 and a presser plate 21 is fitted to a lower end of the compression spring 20. An inflated balloon 22 is fitted to an undersurface of the presser plate 21 and serves as a pressure medium and is sandwiched between the presser plate 21 and a pressure gauge 23 that is fitted to an undersurface of the inflated balloon 22.

The compression spring 20 has a coil diameter (an outer diameter) which is so chosen as to be substantially equal to the diameter of the disc-shaped plate 19. Also the length of the compression spring 20 as measured in a direction conforming to the direction of expansion is so chosen as to be substantially equal to the axial length of the cylindrical member 16.

The presser plate 21 when viewed in a plane has a surface area sufficient to encompass the palm of the patient's hand and the inflated balloon 22 is formed to a size substantially equal to the size of the presser plate 21. The balloon 22 may be made of a rubber material, a soft synthetic resin or a hard synthetic resin. It is, however, to be noted that as the pressure medium in place of the balloon 22, a cushioning member made of a rubber material, a soft synthetic resin or an inorganic plastic material may be employed.

In the pressure regulating device of the structure described above, the box 15 supports an assembly comprised of the adjustment knob 17, the screw rod 18, the disc-shaped plate 19, the compression spring 20, the presser plate 21, the balloon 22 and the pressure gauge 23, all of which are a movable member. This assembly will be hereinafter referred to as a "movable presser unit". The box 15 has a height as measured above the top surface of the heating plate 1 which is so chosen as to allow the cylindrical member 16 and the movable presser unit (excluding the adjustment know 17 and a portion of the screw rod 18) to be completely accommodated within the space of the box 15 and, also, as to permit the hand 2 to be quite naturally inserted in between the heating plate 1 and the pressure gauge 23 when and so long as the disc-shaped plate 19 is held at the uppermost position.

The movable presser unit is arranged so as to occupy a position above the detecting probe 3 and, in particular, the pressure gauge 23 is arranged so as to occupy a position immediately above the detecting probe 3.

The pressure regulating device can be operated in the following manner when in this pressure regulating device utilizing a biasing force of the compression spring 20 the hand is desired to be pressed to such an extent as to permit the pressure of contact of the area to be measured with the detecting probe 3 to be of a predetermined constant value.

While the disc-shaped plate 19 of the pressure regulating device is moved or held at the uppermost position, the hand 2 is inserted inside the box 15 from a rear open area thereof and is subsequently placed at a predetermined position above the heating plate 1, followed by fixing of the hand 2 by means of a positioning device as will be described later. In this way, the hand 2 can be accurately held at the predetermined measuring position by means of the positioning device. At this time, the area of the hand 2 to be measured and the pressure gauge 23 are positioned immediately above the detecting probe 3.

Thereafter, the adjustment knob 17 has to be slowly turned clockwise about the screw rod 18. At this time, although the screw rod 18 is turned together with the adjustment knob 17, the screw rod 18 displaces downwardly a distance corresponding to the amount of rotation of the adjustment knob 17 because of the screw rod 18 threadingly received in the internally threaded hole 24. As a result of the downward shift of the screw rod 18, the movable presser unit (the adjustment knob 17, the screw rod 18, the disc-shaped plate 19, the compression spring 20, the presser plate 21, the balloon 22 and the pressure gauge 23) is edgingly lowered towards the back of the hand. Immediately after the pressure gauge 23 has been brought into contact with the back of the hand, values indicated by the pressure gauge 23 have to be observed.

Further clockwise turning of the adjustment knob 17 brings about contact of the balloon 22 with the back of the hand 2, following the contact of the pressure gauge 23 with the back of the hand, with the back of the hand 2 consequently pressed progressively strongly. At this time, since the balloon 22 tightly contacts the back of the hand regardless of surface irregularities of the back of the hand 2, the hand can be uniformly or evenly pressed. Continued clockwise turning of the adjustment knob 17 will result in increase of the pressure applied to the hand 2, but the clockwise turning of the adjustment knob 17 is interrupted when a pain is felt in the hand 2. It is to be noted that at this time the value indicated by the pressure gauge 23 has exceeded a predetermined preset value. In other words, the preset value is so chosen as to be a value slightly lower than the value at which the pain may be felt in the hand 2.

Thereafter, the adjustment knob 17 has to be turned counterclockwise to lower the pressure applied to the hand 2 while the indication given by the pressure gauge 23 is observed. When the indication of the pressure gauge 23 is lowered down to a value equal to the preset value, the counterclockwise turn of the adjustment knob 17 is interrupted and the biodata measurement is then carried out At this time, the pressure gauge 23 is held immediately above the detecting probe 3 and, hence, the pressure applied to the region (this region being hereinafter referred to as a "pressure measuring region") of the back of the hand 2, which is immediately above the detecting probe 3, that is, immediately above the area to be measured, is kept uniform. Since the pressure measuring region of the back of the hand 2 is located immediately above and opposite to the area to be measured, the pressure at the pressure measuring region is substantially equal to that at the area to be measured. Accordingly, since the pressure at the pressure measuring region of the back of the hand is kept at a predetermined value at all times, the pressure at the area of the palm of the hand to be measured is also kept at a predetermined value and, consequently, the accuracy of measurement of the biodata can be increased.

The reason that the pressure applied to the hand 2 is increased to the value in excess of the preset value and at which the pain is felt in the hand 2 is for the purpose of enhancing the tight contact of the area to be measured with the detecting probe 3. Without employing this technique and if the pressure is progressively increased from a lower value to a value equal to the preset value, there is the possibility that air bubbles may be contained in between the detecting probe 3 and the area to be measured and will therefore impair the accuracy of measurement of the biodata. It is to be noted that since as hereinbefore discussed the detecting probe 5 protrudes about 5 mm upwardly from the top surface of the heating plate 1, the tight contact between the detecting probe 3 and the area to be measured can further be enhanced.

Figure 3:
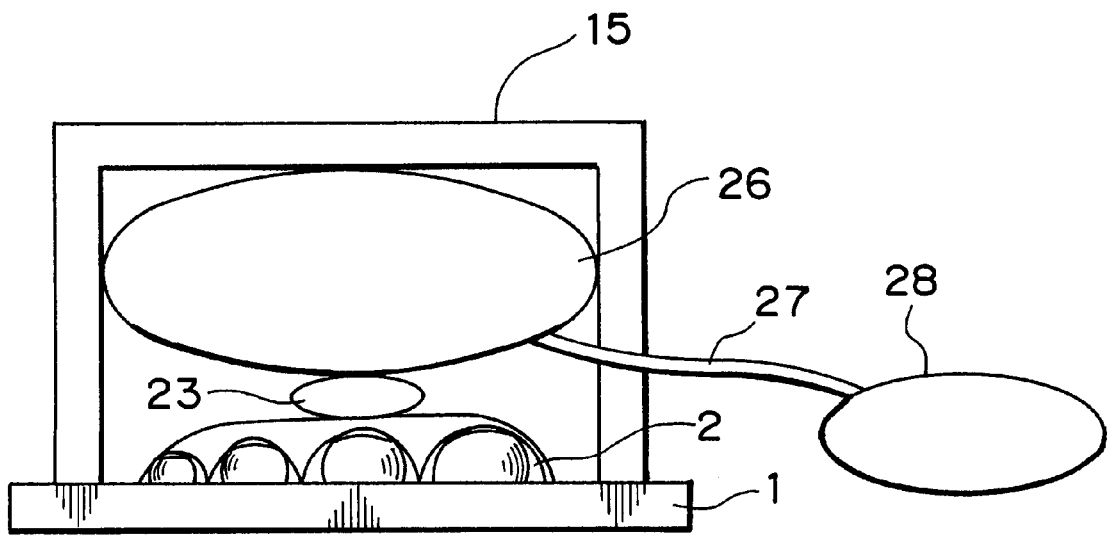
FIG. 3 is a fragmentary sectional view of that portion of a modified form of the pressure regulating device.

Although in the illustrated embodiment the pressure regulating device is of a design wherein the compression spring 20 is utilized to press the hand back, without resorting to this technique a pneumatic pressure may be employed to press the hand back such as shown in FIG. 3. Referring to FIG. 3, an inflatable balloon 26 is employed and is fitted to the undersurface of the top wall of the box 15. This balloon 26 is communicated with an air pump 28 through a tube 27. The air pump 28 is of a type capable of selectively pumping air into or from the balloon 26. The pressure gauge 23 is fitted to an undersurface area of the balloon 26. It is to be noted that balloon 26 when inflated is of a size sufficient to cover the hand in its entirety. It is also to be noted that so long as the balloon 26 is of a size sufficiently accommodated inside the box 15, the balloon 26 when inflated may partly protrude outwardly from the box 15 through one or both of the front and rear open areas. This balloon 26 is positioned above the detecting probe 3 and particularly the pressure gauge 23 is positioned immediately above the detecting probe 3.

The pressure regulating device of the type wherein the pneumatic pressure is utilized can be operated generally in the following manner, in order for the hand 2 to be pressed under a predetermined pressure applied to the area to be measured which is held in contact with the detecting probe 3.

While the balloon 26 is deflated, the hand 2 is to be positioned at a predetermined measuring site by means of the positioning device in a manner similar to that effected with the pressure regulating device utilizing the biasing force of the compression spring 20. At this time the area of the hand 2 to be measured and the pressure gauge 23 are positioned immediately above the detecting probe 3.

The air pump 28 is operated to supply air to the balloon 26 to inflate the latter. As the balloon 26 is inflated, the undersurface area of the balloon 26 and the pressure gauge 23 are edgingly shifted downwardly towards the back of the hand 2. Immediately after the pressure gauge 23 is brought into contact with the back of the hand, values indicated by the pressure gauge 23 have to be observed.

Further supply of the air to the balloon 26 brings about contact of the balloon 26 with the back of the hand 2, following the contact of the pressure gauge 23 with the back of the hand, with the back of the hand 2 consequently pressed progressively strongly with increase of a pneumatic pressure inside the balloon 26. At this time, since the balloon 26 tightly contacts the back of the hand regardless of surface irregularities of the back of the hand 2, the hand can be uniformly or evenly pressed. The supply of the air to the balloon 26 is interrupted when a pain is felt in the hand 2. It is to be noted that at this time the value indicated by the pressure gauge 23 has exceeded the predetermined preset value.

Thereafter, the air pump is operated to discharge the air inside the balloon 26 to deflate the latter (to lower the pressure inside the balloon 26) to thereby reduce the pressure applied to the hand 2, while the indication given by the pressure gauge 23 is observed. When the indication of the pressure gauge 23 is lowered down to a value equal to the preset value, the discharge of the air from the balloon 26 is interrupted and the biodata measurement is then carried out.

At this time, the pressure gauge 23 is held immediately above the detecting probe 3 and, hence, the pressure applied to the pressure measuring region of the back of the hand 2, which is immediately above the detecting probe 3, that is, immediately above the area to be measured, is kept uniform. Since the pressure measuring region of the back of the hand 2 is located immediately above and opposite to the area to be measured, the pressure at the pressure measuring region is substantially equal to that at the area to be measured. Accordingly, as is the case with the pressure regulating device utilizing the biasing force of the compression spring 20, the pressure at the pressure measuring region of the back of the hand is kept at a predetermined value at all times and, therefore, the pressure at the area of the palm of the hand to be measured is also kept at a predetermined value and, consequently, the accuracy of measurement of the biodata can be increased.

The reason that the pressure applied to the hand 2 is increased to the value in excess of the preset value and at which the pain is felt in the hand 2 is similar to that described hereinbefore in connection with the pressure regulating device utilizing the biasing force of the compression spring 20.

Where with the pressure regulating device utilizing either the biasing force of the compression spring 20 or the pneumatic pressure, the biodata measurement is carried out while the pressure applied to the pressure measuring region of the back of the hand is kept uniform, the biodata measurement is carried out while the area to be measured contains a blood component since the blood circulates in the hand 2. However, it often occurs that the biodata measurement requires no blood component present in the area to be measured. In view of this, with the pressure regulating device of the present invention, the biodata measurement can be carried out in the following manner with no blood component present in the area to be measured.

Where the pressure regulating device utilizing the biasing force of the compression spring 20 is employed, after the hand 2 has been positioned at the predetermined measuring site, the adjustment knob 17 has to be sufficiently turned clockwise to increase the pressing force applied to the hand 2 to such a value that the blood no longer circulates in a region of the hand 2 adjacent the palm. On the other hand, where the pressure regulating device utilizing the pneumatic pressure is employed, after the hand 2 has been positioned at the predetermined measuring site, the air pump 28 has to be operated to increase the pneumatic pressure inside the balloon 26 sufficiently to such a value that the blood no longer circulate in the region of the hand 2 adjacent the palm.

Thus, with the optical biodata measuring apparatus provided with the pressure regulating device of the present invention, the biodata can be accurately measured with the single apparatus either under a condition in which the blood component is contained in the area to be measured or under a condition in which no blood component is contained in the area to be measured.

Figure 12:
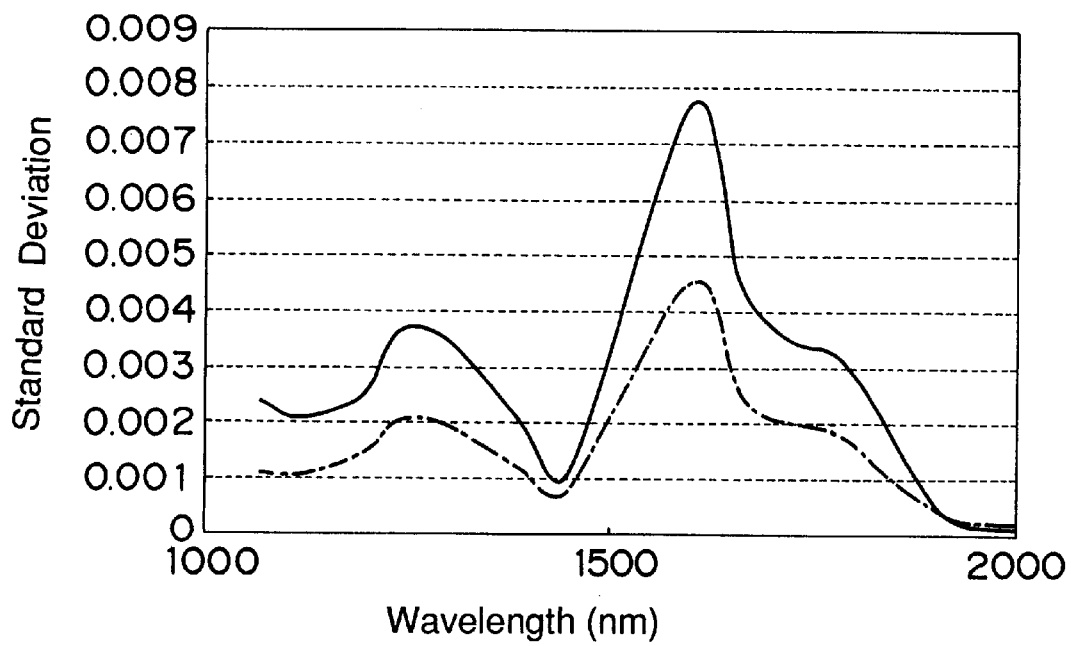
FIG. 12 is a graph showing standard deviations between the measured biodata obtained with and without the use of the pressure regulating device, respectively.

Respective results of the actually performed biodata measurement with and without the pressure regulating device employed are shown in FIG. 12. During the biodata measurement, the bundled optical fiber was employed to irradiate the area to be measured, i.e., that portion of the palm of a subject, with infrared light and the spectrum of the light reflected from the area to be measured was measured. In carrying out while the biodata measurement, the infrared region of light was employed, the subject's hand was cyclically placed 15 times and the measurement was carried out each time the hand was placed. Standard deviations obtained from those measurement data are shown in the graph of FIG. 12.

It is clear from the graph of FIG. 12 that the standard deviation at most of the wavelength regions is smaller with the case in which the pressure regulating device of the present invention as shown by the single-dotted line was employed than with the case in which no pressure regulating device was employed as shown by the solid line. More specifically, where the pressure regulating device of the present invention is employed, it can be said that the hand can be accurately placed at the predetermined measuring site and that variation in resultant data is consequently minimized to accomplish a considerably high reproducibility of the measured values.

The optical biodata measuring apparatus of the present invention is also provided with the positioning device (position regulating device) with which the hand 2 can be fixed at the predetermined measuring site on the heating plate 1 so that the area to be measured can be accurately positioned relative to the detecting probe 3. The structure and the function of the positioning device will now be described with particular reference to FIGS. 4 and 5.

Figure 4:
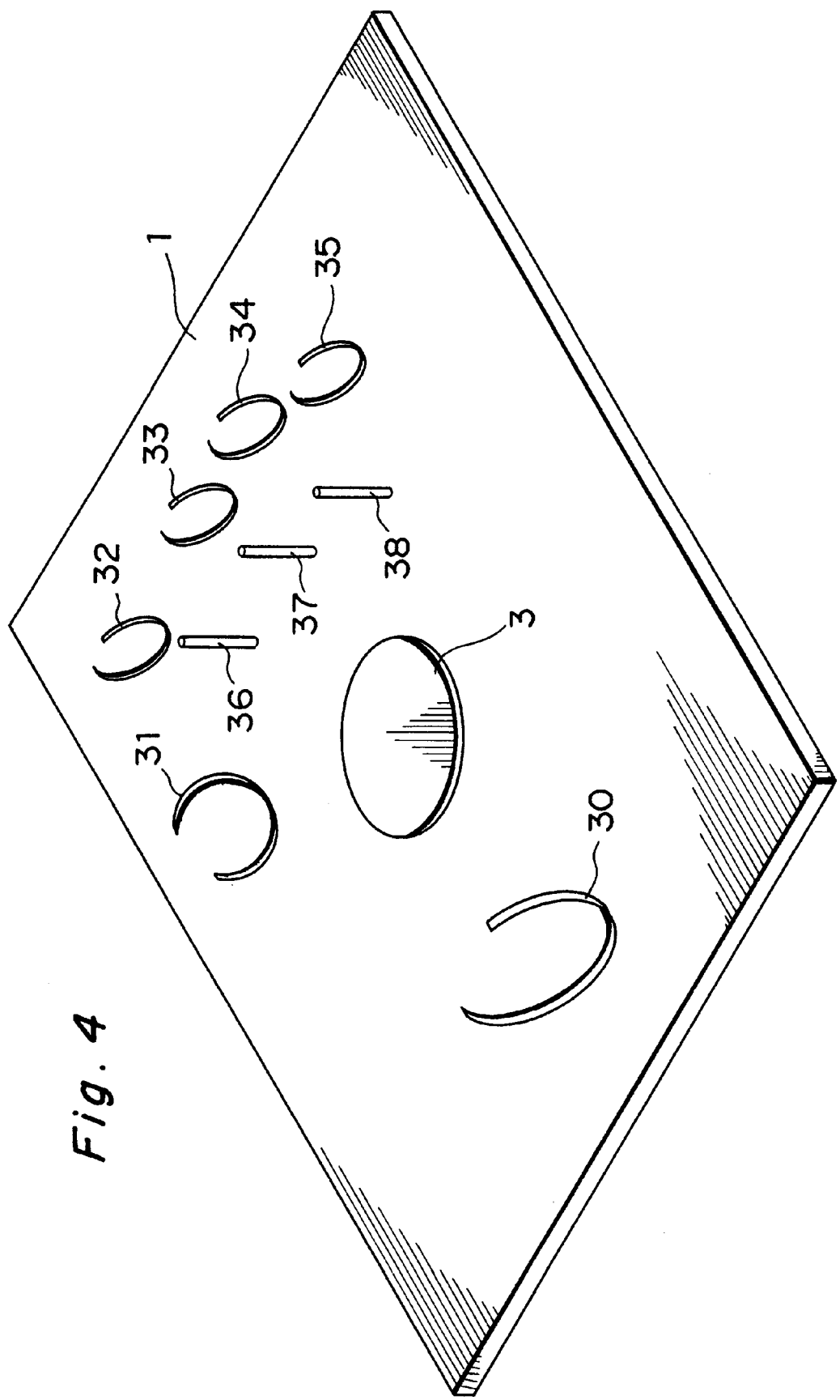
FIG. 4 is a schematic perspective view showing a positioning device used in the biodata measuring apparatus.
Figure 5:
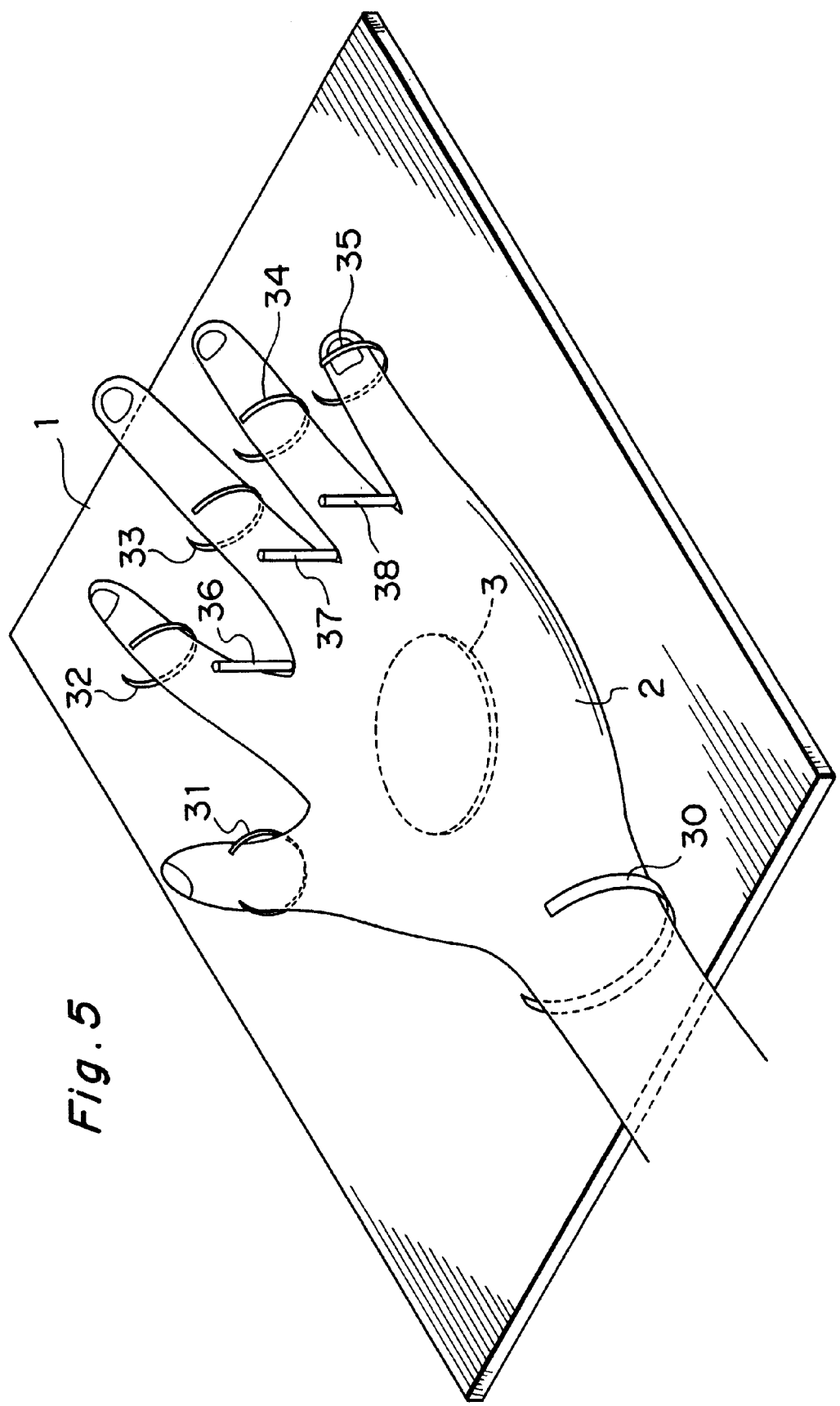
FIG. 5 is a view similar to FIG. 4, showing a hand having been positioned at a predetermined measuring site by the positioning device.

FIG. 4 illustrates a schematic perspective view of the positioning device of the present invention and FIG. 5 illustrates a condition in which the hand 2 is fixedly positioned on the heating plate 1 by means of the positioning device shown in FIG. 4.

As shown in FIGS. 4 and 5, the positioning device comprises a generally C-shaped wrist holder ring 30 in the form of a split ring for holding the wrist, generally C-shaped first to fifth finger holder rings 31, 32, 33, 34 and 35, each also in the form of a split ring, for holding thumb, index, middle, ring and little fingers, respectively, and first to third arresting poles 36, 37 and 38 each engageable with the bottom of a generally V-shaped crevice delimited between the index and middle fingers, between the middle and ring fingers or between the ring and little fingers, respectively, all being mounted on the heating plate 1. Each of the holder rings 30 to 35 has a split region appearing in the circumference of the respective holder ring, and the presence of such split region is mainly intended to facilitate insertion of the wrist or finger through the respective holder ring at the time the hand 2 is desired to be fixedly positioned.

The wrist holder ring 30 is fixedly mounted on the heating plate 1, with the split region oriented upwardly, at such a location as to align with the wrist when the hand 2 is placed at the predetermined measuring site above the heating plate 1. Similarly, each of the first to fifth finger holder rings 31 to 35 is fixedly mounted on the heating plate 1, with the split region oriented upwardly, at such a location as to align with an intermediate portion of the thumb, index, middle, ring or little finger when the hand 2 is placed at the predetermined measuring site above the heating plate 1.

Figure 6A:
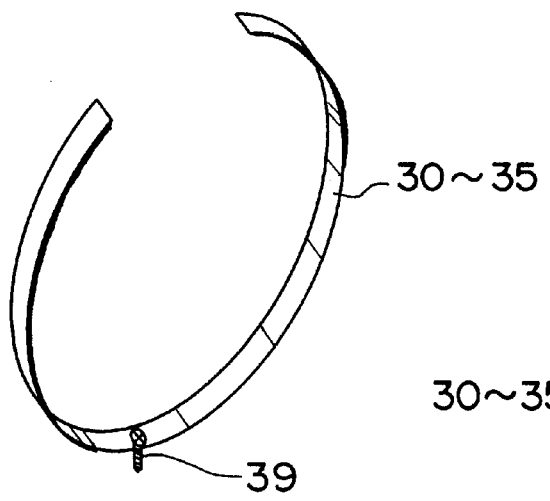
FIG. 6A is a perspective view of one of holder rings employed in the positioning device.

More specifically, as shown in FIG. 6A, a portion of each of the holder rings 30 to 35 which is substantially diametrically opposite to the respective split region and which is held in contact with the heating plate 1 has a set screw 39 secured thereto. Accordingly, each of the holder rings 30 to 35 can be fixedly mounted on the heating plate 1 by threadingly engaging the set screw 39 in an internally threaded hole (not shown) defined in the heating plate 1.

Figure 6B:
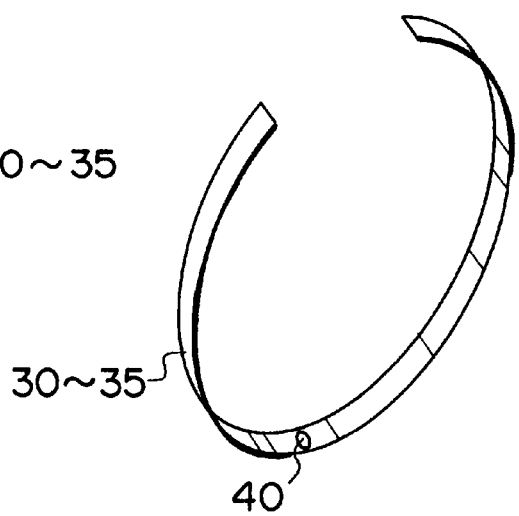
FIG. 6B is a view similar to FIG. 6A, showing a modified form of the holder ring.

Alternatively, as shown in FIG. 6B, that portion of each of the holder rings 30 to 35 which is substantially diametrically opposite to the respective split region and which is held in contact with the heating plate 1 may have a perforation 40 defined therein so that a screw member can be passed through the perforation in each holder ring 30 to 35 and then threadingly engaged in a corresponding internally threaded hole (not shown) in the heating plate 1 to thereby secure the respective holder ring to the heating plate 1.

Although not shown, each holder ring 30 to 35 may be fixedly mounted on the heating plate 1 by means of a pin either connected to or separate from the respective holder ring, which pin is inserted into a corresponding hole defined in the heating plate 1.

Each of the first to third arresting poles 36 to 38 is fixedly mounted on the heating plate 1 at such a location that the respective arresting pole 36 to 38 can engage the bottom of the generally V-shaped crevice between the index and middle fingers, between the middle and ring fingers or between the ring and little fingers, respectively. Also, each of the first to third arresting poles 36 to 38 has a height above the heating plate 1 that is somewhat lower than the thickness of the hand 2 placed on the heating plate 1.

Figure 7A:
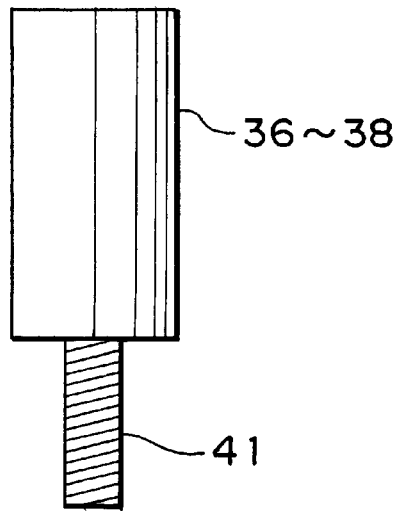
FIG. 7A is a side view of one of arresting poles employed in the positioning device.
Figure 7B:
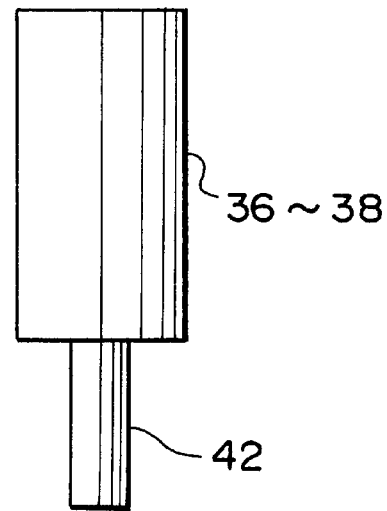
FIG. 7B is a view similar to FIG. 7A, showing a modified form of the arresting pole.

To connect each of the first to third arresting poles 36 to 38, as shown in FIG. 7A, each arresting pole has a lower end formed with a coaxial screw member 41 that is threadingly engaged in a corresponding internally threaded hole (not shown) defined in the heating plate 1 to fixedly mount the respective arresting pole on the heating plate 1. Alternatively, as shown in FIG. 7B, each arresting pole may have that lower end formed with a coaxial stud pin 42 of a diameter smaller than the respective arresting pole, which stud pin 42 is press-fitted into a corresponding hole (not shown) defined in the heating plate to thereby fixedly mount the respective arresting pole on the heating plate 1.

In the meantime, the size of the hand from which the biodata is measured varies from a subject to another and, therefore, the use of the holder rings 30 to 35 and the arresting poles 36 to 38 requires them to be repositioned on the heating plate 1 to accommodate a different size of the hand. Accordingly, in the positioning device in the illustrated embodiment, the plurality of the internally threaded holes (or the holes in the case of the pins) for securing the holder rings 30 to 35 and the arresting poles 36 to 38 are formed in the heating plate 1 in a predetermined pattern (for example, equally spaced a few millimeters or in a square arrangement). Accordingly, the holder rings 30 to 35 and the arresting poles 36 to 38 can be repositioned at respective positions encompassed within the predetermined pattern of the internally threaded holes as desired.

Accordingly, when the biodata measurement is to be carried out with respect to a certain subject, and in the event that one or some of the holder rings 30 to 35 and arresting poles 36 to 38 are deviated from the aforesaid predetermined position, only the holder rings and arresting poles which are deviated have to be removed from the heating plate 1 by undoing screws and repositioned at respective locations matching with or closest to the positions where they ought to have occupied.

Also, if the proper internally threaded holes for securing the holder rings 30 to 35 and arresting poles 36 to 38 are once set in the heating plate 1 for a certain subject and the respective positions of the internally threaded holes are recorded, the record can be advantageously utilized to adjust, modify or reposition the holder rings 30 to 35 and arresting poles 36 to 38 at respective locations proper to such certain subject even though the respective positions of the holder rings 30 to 35 and arresting poles 36 to 38 have once been changed by some reason.

Each of the holder rings 30 to 35 is made of a flexible material. The wrist holder ring 30 is shaped to a size slightly smaller than the wrist to be held thereby, and each of the first to fifth finger holder rings 31 to 35 is shaped to a size slightly smaller than the respective finger to be held thereby. Since each of the holder rings 30 to 35 is made of the flexible material as described above, and even though each of the holder rings 30 to 35 is shaped to a size slightly smaller than the wrist or finger to be held thereby, the wrist or the respective finger can easily be inserted and held thereby. Also, the wrist or each finger can fit tightly in the associated holder ring 30 to 35 and can therefore be constrained firmly at the required position.

Examples of the material for the holder rings 30 to 35 include, for example, a rubber material, a soft synthetic resin, an inorganic plastic material and a metallic material. A shape memory alloy may also be used as a material for the holder rings 30 to 35.

Specific examples of the material for the arresting poles 36 to 38 include, for example, a rubber material, a soft synthetic resin, a hard synthetic resin, an inorganic plastic material and a metallic material.

With the use of the positioning device of the structure discussed above, the hand 2 can be placed, i.e., fixed or positioned at the predetermined measuring site in the following manner.

The wrist has to be held by the wrist holder ring 30 and the fingers have to be held in the associated first to fifth finger holder rings 31 to 35. Thereafter, the hand 2 should be slid forwards until the first to third arresting poles 36 to 38 are brought into contact with the respective bottoms of the V-shaped crevices between the index and middle fingers, between the middle and ring fingers and between the ring and little fingers, respectively.

In the condition in which the first to third arresting poles 36 to 38 are engaged with the respective bottoms of the V-shaped crevices between the index and middle fingers, between the middle and ring fingers and between the ring and little fingers, respectively, the hand 2 can be constrained by those arresting poles 36 to 38 from displacing forwards or rearwards and the hand 2 can also be constrained by the holder rings 30 to 35 from displacing in a direction laterally thereof. Thus, the hand 2 can be firmly fixed or positioned accurately at the predetermined measuring site on the heating plate 1.

Since the holder rings 30 to 35 and the arresting poles 36 to 38 are arranged at the predetermined locations on the heating plate 1 and the hand 2 can be positioned at the predetermined site above the heating plate 1, the detecting probe 3 can be held accurately in contact with the same area of the palm of the hand 2, that is, the area to be measured at all times.

Although in the positioning device of the structure described above the lateral displacement of the hand 2 is inhibited by the holder rings 30 to 35, the present invention may not be limited thereto and a press unit may be employed which comprises combinations of a fixed plate and a movable plate to press and sandwich the wrist or each finger to thereby avoid any possible lateral displacement of the hand 2. The alternative positioning device provided with the press units is shown in a perspective view in FIG. 8, and the manner of use of the press units to constrain the respective fingers of the hand 2 is shown in FIG. 9.

Figure 9:
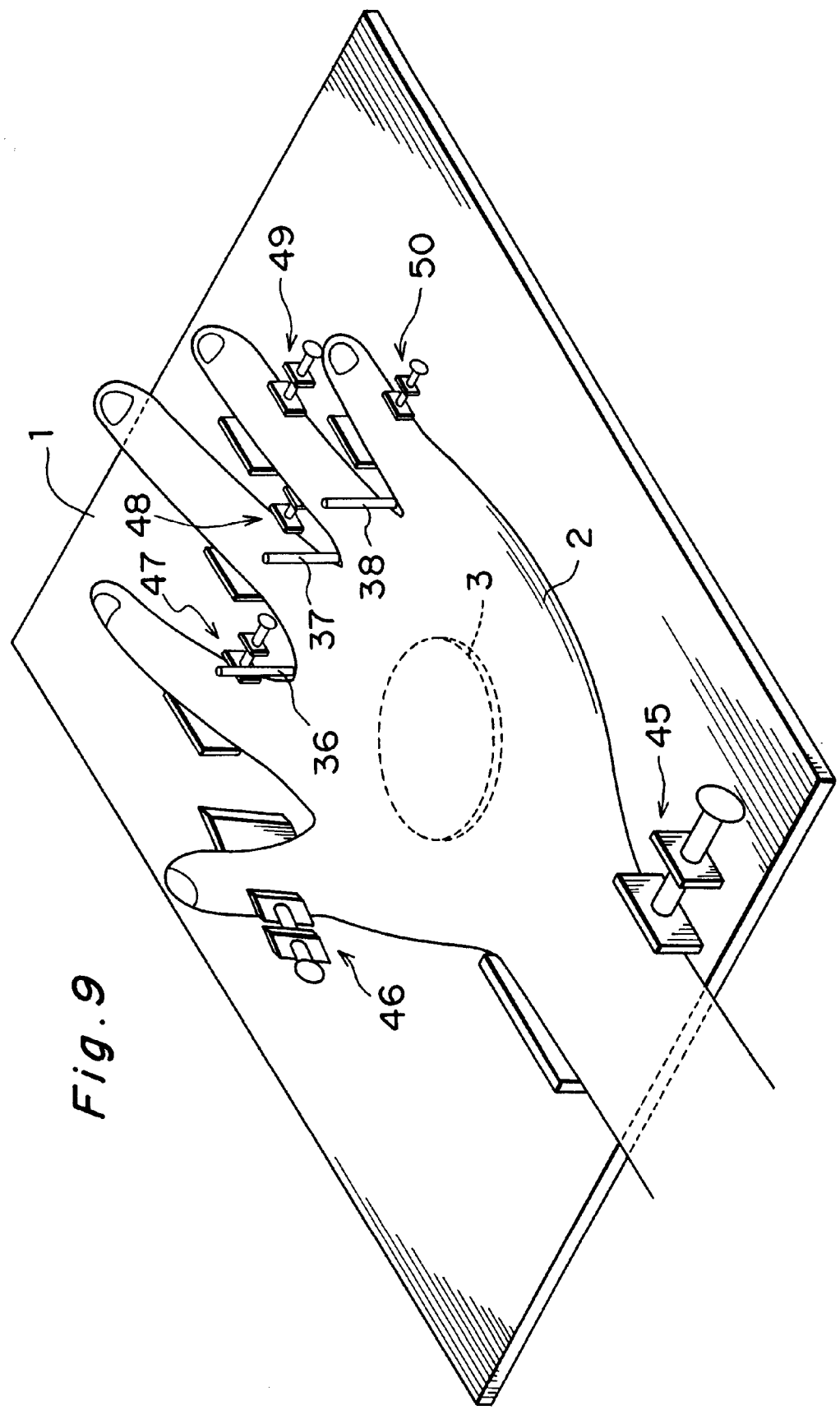

Referring to FIGS. 8 and 9, the alternative positioning device shown therein comprises a wrist press unit 45 for pressing and sandwiching the wrist, and first to fifth press units 46 to 50 for pressing and sandwiching the thumb, index, middle, ring and little fingers, respectively, of the hand 2, in combination with the first to third arresting poles 36 to 38 which function in the manner described hereinbefore.

The wrist press unit 45 is fixedly mounted on the heating plate 1 at such a location as to align with the wrist when the hand 2 is placed at the predetermined measuring site above the heating plate 1. Similarly, each of the first to fifth finger press units 46 to 50 is fixedly mounted on the heating plate 1 at such a location as to align with an intermediate portion of the thumb, index, middle, ring or little finger when the hand 2 is placed at the predetermined measuring site above the heating plate 1.

Figure 10:
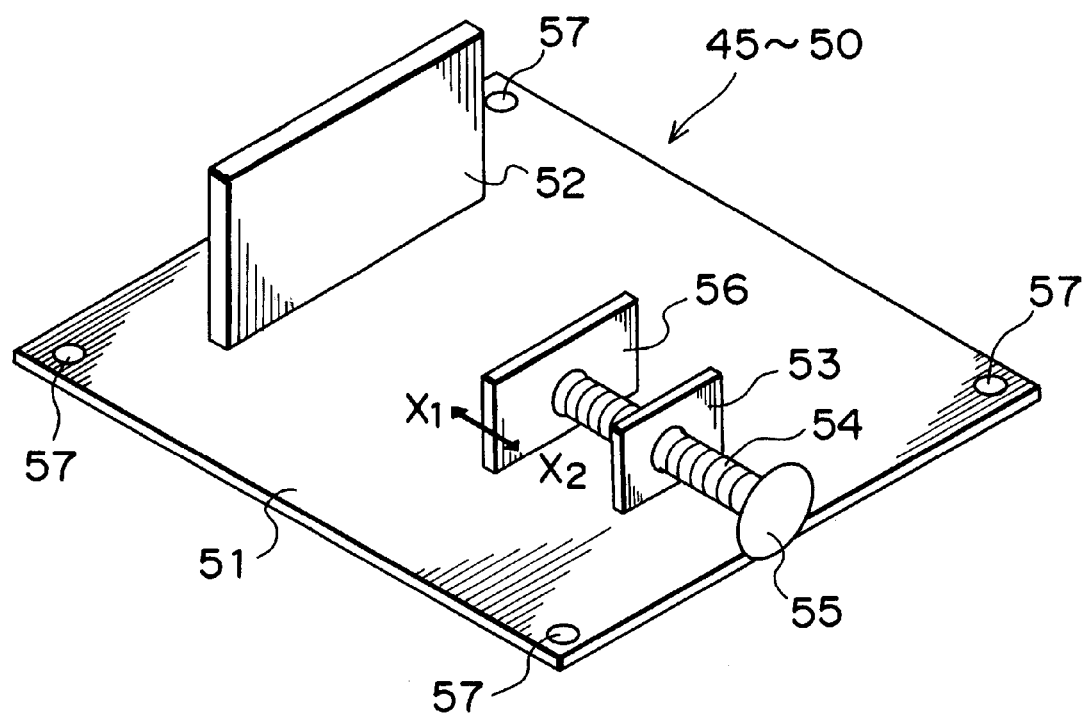
FIG. 10 is a perspective view, on an enlarged scale, showing one of pressing units employed in the modified positioning device shown in FIG. 8.

As shown in FIG. 10, each of the press units 45 to 50 includes a base plate (a press unit fixing plate) 51 having a plurality of, for example, four, screw holes 57 for securing the base plate 51 to the heating plate 1 by means of respective set screws (not shown), a fixed plate 52 fixedly mounted on the base plate 51 at a predetermined position, and a movable plate support member 53 also fixedly mounted on the base plate 51 at a location spaced from the fixed plate 52. The movable plate support member 53 is formed with an internally threaded hole 57 through which an adjustment screw 54 is threadingly received. The adjustment screw 54 has its longitudinal axis lying perpendicular to a plane of the fixed plate 52, and a movable plate 56 is secured to one end of the respective adjustment screw 54 adjacent the fixed plate 52. The opposite end of the respective adjustment screw 54 is provided with a knob 55. It is to be noted that the movable plate 56 connected with the adjustment screw 54 confronts and lies parallel to the plane of the fixed plate 52. Although not shown, one of opposite surfaces of each of the fixed and movable plates 52 and 56 which is held in contact with the wrist or finger is lined with a cushioning material to protect the wrist or finger.

In each of the press units 45 to 50, when the knob 55 is turned clockwise, the adjustment screw 54 and the knob 55 displace or advance together with the movable plate 56 in a direction shown by the arrow X1 since the adjustment screw 54 threadingly received in the internally threaded holes in the associated movable plate support member 53, with the movable plate 56 consequently moved towards the fixed plate 52. On the other hand, when the knob 55 is turned counterclockwise, the adjustment screw 54 and the knob 55 displace or retract together with the movable plate 56 in a direction shown by the arrow X2, with the movable plate 56 consequently separated away from the fixed plate 52. Accordingly, when and after the wrist or finger is placed in between the fixed and movable plates 52 and 56 and the knob 55 is subsequently turned clockwise, the wrist or finger can be pressed and sandwiched by the movable plate 56 cooperating with the fixed plate 52. The pressure under which the wrist or finger is sandwiched between the fixed and movable plates 52 and 56 can be adjusted by finely adjusting the knob 55, i.e., finely turning the knob 55 clockwise or counterclockwise.

Although in each of the press units 45 to 50 discussed above the fixed and movable plates 52 and 56 have been described and shown as lying parallel to each other, they may be laid so as to converge in a direction upwardly of the respective base plate 51 such that the space between respective upper edges of the fixed and movable plates 52 and 56 is smaller than the space between respective lower edges thereof. This arrangement is particularly advantageous in that the wrist or finger can be tightly held in position with the fixed and movable plates 52 and 55 tightly contacting it while the wrist or finger is urged downwardly to tightly contact the heating plate 1.

To change the position of each of the press units 45 to 50 on the heating plate 1, the base plate 51 of the respective press unit has to be removed from the heating plate 1 by undoing the set screws and then reposition it to a different location on the heating plate 1 with the set screws again fastened to the heating plate 1. The heating plate 1 has a plurality of screw holes defined therein in a predetermined pattern for threadingly receiving the respective set screws used to secure the base plates 51 of the press units 45 to 50 to the heating plate 1. Accordingly, the press units 45 to 50 can be repositioned on the heating plate 1 at respective locations encompassed by the pattern of arrangement of the screw holes.

Although in each of the press units 45 to 50 the movable plate 56 can be moved to press the wrist or finger against the fixed plate 52 by turning the knob 55, the present invention is not limited thereto. For example, a biasing spring operable to normally urge the movable plate 56 towards the fixed plate 52 may be employed so that the wrist or finger can be pressed and sandwiched between the fixed and movable plates 52 and 56 by the effect of the biasing force of the spring. In such case, in order to assuredly fix the wrist or finger in position, the biasing spring for each press unit must be of a type capable of exerting the sufficiently high biasing force.

Figure 13:
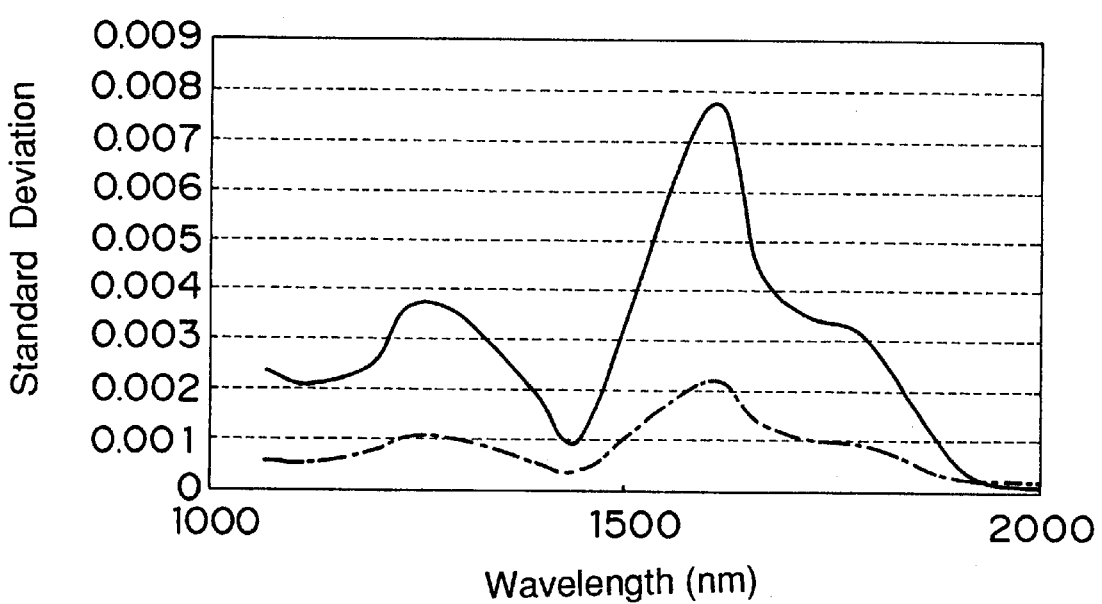
FIG. 13 is a graph showing standard deviations between the measured biodata obtained with and without the use of the positioning device, respectively.

Respective results of the actually performed biodata measurement with and without the positioning device employed are shown in FIG. 13. During the biodata measurement, the bundled optical fiber was employed to irradiate the area to be measured, i.e., that portion of the palm of a subject, with near infrared light and the spectrum of the light reflected from the area to be measured was measured. In carrying out while the biodata measurement, the infrared region of light was employed, the subject's hand was cyclically placed 15 times and the measurement was carried out each time the hand was placed. Standard deviations obtained from those measurement data are shown in the graph of FIG. 13.

It is clear from the graph of FIG. 13 that the standard deviation at most of the wavelength regions is smaller with the case in which the positioning device of the present invention as shown by the single-dotted line was employed than with the case in which no positioning device was employed as shown by the solid line. More specifically, where the pressure regulating device of the present invention is employed, it can be said that the hand can be accurately placed at the predetermined measuring site and that variation in resultant data is consequently minimized to accomplish a considerably high reproducibility of the measured values.

Although the present invention has been described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A positioning device for fixing a hand of a person relative to a measuring probe during a biodata measurement, said positioning device comprising:

a support plate, said measuring probe being mounted on the support plate with a portion thereof protruding a slight distance outwardly from a surface of the support plate, said support plate adapted to support the person's hand thereon with a target area of a palm of the person's hand overlaying the portion of the measuring probe during the biodata measurement;

a plurality of local fixing members mounted on the surface of the support plate for fixing respective fingers of the person's hand, said local fixing members being positioned generally radially outwardly from the measuring probe and at respective locations selected to allow the target area of the person's palm to be held immovably in contact with the portion of the measuring probe during the biodata measurement, each of said local fixing members being operable to apply a pressure to the corresponding finger to retain such finger as fixed thereby; and a wrist fixing member mounted on the surface of the support plate and positioned generally outwardly from the measuring probe and on a side of the measuring probe opposite to the plurality of local fixing members for fixing a person's wrist when the person's hand is placed on the support plate, said wrist fixing member being operable to apply a pressure to the wrist to retain such wrist as fixed thereby.

2. The device as claimed in claim 1, further comprising an arresting pole mounted on the surface of the support plate at a location corresponding to the bottom of a generally V-shaped crevice delimited between the neighboring fingers other than the thumb for constraining the person's hand from a possible displacement in a direction in which the fingers are inserted along the surface of the support plate.

3. The device as claimed in claim 2, wherein each of the local fixing members comprises a generally elastically deformable C-shaped holder ring for fixedly holding the corresponding finger by application of a pressure therefrom to the corresponding finger in a direction generally radially inwardly thereof and wherein the wrist fixing member comprises a generally elastically deformable C-shaped holder ring for fixedly holding the wrist by application of a pressure therefrom to the wrist in a direction generally radially inwardly thereof.

4. The device as claimed in claim 3, wherein each of the holder rings is made of a material selected from the group consisting of a rubber material, a metallic material, a soft synthetic resin, a hard synthetic resin and an inorganic plastic material.

5. The device as claimed in claim 2, wherein each of the local fixing members comprises a pressing unit including a fixed plate and a movable plate movable towards the fixed plate to sandwich the corresponding finger between the fixed and movable plates.

6. The device as claimed in claim 2, wherein the arresting pole is made of a material selected from the group consisting of a rubber material, a metallic material, a soft synthetic material, a hard synthetic material and an inorganic plastic material.

7. The device as claimed in claim 1, wherein each of the local fixing members is repositionable relative to the support plate.

8. A method of positioning a person's hand relative to a detecting probe during a biodata measurement with the use of a positioning device which comprises a support plate, said measuring probe being mounted on the support plate with a portion thereof protruding a slight distance outwardly from a surface of the support plate, a plurality of local fixing members mounted on the surface of the support plate and positioned generally radially outwardly from the measuring probe and at respective locations; and a wrist fixing member mounted on the surface of the support plate and positioned generally radially outwardly of the measuring probe and on one side from the measuring probe opposite to the plural local fixing members, said method comprising the steps of:

placing the person's hand thereon with a target area of a palm of the person's hand overlaying the portion of the measuring probe during the biodata measurement;

fixing the fingers relative to the support surface by means of the local fixing members to allow the target area of the person's palm to be held immovably in contact with the portion of the measuring probe during the biodata measurement by applying a pressure from each local fixing member to the corresponding finger to retain such finger as fixed thereby; and fixing the person's wrist relative to the support surface by means of the wrist fixing member by applying a pressure to the wrist to retain such wrist as fixed thereby.

* * * * *

UNITED STATES PATENT AND TRADEMARK OFFICE
CERTIFICATE OF CORRECTION

PATENT NO. : 6,101,405
DATED : August 8, 2000
INVENTOR(S) : Nobuyoshi YASUDA et al.

Page 1 of 1

It is certified that error appears in the above-identified patent and that said Letters Patent is hereby corrected as shown below:

On title page,
In category [30] Foreign Application Priority Data", please change the priority date from "Jun. 8, 1997" to --August 6, 1997--.

Signed and Sealed this

Fifth Day of June, 2001

*Attest:*

*Attesting Officer*

NICHOLAS P. GODICI
*Acting Director of the United States Patent and Trademark Office*